United States Patent
Li et al.

(10) Patent No.: US 7,439,405 B1
(45) Date of Patent: Oct. 21, 2008

(54) PURIFICATION OF PROPYLENE GLYCOL MONOALKYL ETHER

(75) Inventors: Xiangmin Li, Glen Mills, PA (US); Lawrence M. Candela, Havertown, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 12/008,759

(22) Filed: Jan. 14, 2008

(51) Int. Cl.
*C07C 41/36* (2006.01)
*C07C 41/34* (2006.01)

(52) U.S. Cl. .................................................. 568/699

(58) Field of Classification Search ................... 568/699
See application file for complete search history.

(56) References Cited

U.S. PATENT DOCUMENTS 2,327,053 A   8/1943   Marple et al.

FOREIGN PATENT DOCUMENTS

GB   271169   5/1927

*Primary Examiner*—Elvis O Price
(74) *Attorney, Agent, or Firm*—Kevin M. Carroll

(57) ABSTRACT

The invention is a method of purifying a propylene glycol monoalkyl ether containing carbonyl impurities which comprises contacting the propylene glycol monoalkyl ether stream in the liquid phase with a carbon adsorbent, and recovering a purified propylene glycol monoalkyl ether product. The purification method improves product quality and reduces the amount of carbonyl impurities in the propylene glycol monoalkyl ether.

9 Claims, No Drawings

PURIFICATION OF PROPYLENE GLYCOL MONOALKYL ETHER

FIELD OF THE INVENTION

This invention relates to the purification of a propylene glycol monoalkyl ether.

BACKGROUND OF THE INVENTION

Propylene glycol monoalkyl ethers are high-performance industrial solvents for paints and coatings, cleaners, inks, and a variety of other applications, including agricultural, cosmetic, electronic, textile, and adhesive products. They are also used as chemical intermediates for end-products such as propylene glycol ether acetates.

Typically, propylene glycol monoalkyl ethers are formed by the reaction of propylene oxide with an alcohol, such as methanol or 1-butanol. Although a catalyst is not required, the reaction is typically performed in the presence of a catalyst. A wide variety of catalysts and reaction conditions are taught in the prior art.

The catalysts used in this process include acidic, basic, and neutral species. Particularly useful catalysts include acids such as sulfuric acid, boric acid and some fluorine-containing acids; or bases such as alkali and alkaline earth metal hydroxides and alkoxides, tertiary amines, and certain metal oxides. G.B. Pat. No. 271,169, for instance, discloses the use of sulfuric acid, alkali metal alkoxides, and alkali metal salts of lower fatty acids. U.S. Pat. No. 2,327,053 teaches the use of metal halides such as stannic halides, antimony pentahalides, aluminum halides, zinc halides and ferric halides.

A problem associated with these reactions, and in particular the use of alkali or alkaline earth metal alkoxide catalysts, is that the propylene glycol monoalkyl ether product is contaminated with various carbonyl impurities (such as formaldehyde, acetaldehyde, propionaldehyde, acetone, methoxy acetone, and methoxy butenone) that lead to high UV absorption. In the production of propylene glycol monoalkyl ethers, the product is typically purified by distillation methods. However, distillation fails to remove a significant portion of the carbonyl impurities. For particular applications, it may be necessary to limit the amount of carbonyl impurities and thus lower the UV absorbance of the propylene glycol monoalkyl ether product.

In sum, new methods for the purification of propylene glycol monoalkyl ethers are needed. Particularly useful methods will decrease the amount of carbonyl impurities and thus improve the UV absorbance and color of the propylene glycol monoalkyl ether product. We have discovered an effective, convenient method to purify propylene glycol monoalkyl ethers.

SUMMARY OF THE INVENTION

The invention is a method of purifying a propylene glycol monoalkyl ether which contains carbonyl impurities. The method comprises contacting the propylene glycol monoalkyl ether in the liquid phase with a carbon adsorbent, and recovering a purified propylene glycol monoalkyl ether product having a decreased carbonyl impurities content. The method reduces the aldehyde and ketone impurity level and UV absorbance in the propylene glycol monoalkyl ether.

DETAILED DESCRIPTION OF THE INVENTION

Propylene glycol monoalkyl ether, as produced commercially, contains small but significant amounts of carbonyl impurities. For example, the total amount of carbonyl impurities contained in a propylene glycol monoalkyl ether product stream are typically greater than 50 ppm, giving the propylene glycol monoalkyl ether product a UV absorbance (at 245 nm) of greater than 1. The propylene glycol monoalkyl ethers to be treated by the method of the invention illustratively comprise about 50 to 20,000 ppm, and usually about 50 to 1,000 ppm, by weight of various carbonyl impurities. The carbonyl impurities include formaldehyde, acetaldehyde, propionaldehyde, acetone, methoxy acetone, and methoxy butenone.

The propylene glycol monoalkyl ether that is purified by the method of the invention is preferably produced by reacting propylene oxide with an alcohol in the presence of an alkali or alkaline earth metal alkoxide to produce a reaction product mixture comprising propylene glycol monoalkyl ether. The reaction product mixture is then subjected to one or more distillation steps in order to produce the propylene glycol monoalkyl ether.

The alcohol used in the production of propylene glycol monoalkyl ether is suitably an aliphatic, cycloaliphatic or an aromatic alcohol and may have one, two, or more hydroxyl groups. Most preferably, the alcohol is a $C_1$-$C_4$ alcohol, particularly, methanol, ethanol, 1-propanol, 2-propanol, 1-butanol, and tert-butanol. Although any alkali or alkaline earth metal alkoxides may be used, alkali metal alkoxides are preferred and potassium alkoxides and sodium alkoxides are particularly preferred. Preferred sodium alkoxides include sodium methoxide, ethoxide, n-propoxide, n-butoxide, and t-butoxide. Preferred potassium alkoxides include potassium methoxide, ethoxide, n-propoxide, and n-butoxide, and t-butoxide.

There are two propylene glycol monoalkyl ether isomers, 1-alkoxy-2-propanol and 2-alkoxy-1-propanol, that are produced in this reaction. For instance the reaction of propylene oxide and methanol produces both 1-methoxy-2-propanol (known as "PM-1") and 2-methoxy-1-propanol ("PM-2"). PM-1, the major product from methanol propoxylation, is the isomer sold commercially. Propylene glycol monoalkyl ethers are available from Lyondell Chemical Company as ARCOSOLV® propylene glycol ethers, such as ARCOSOLV PM (propylene glycol monomethyl ether), ARCOSOLV PNB (propylene glycol normal butyl ether), ARCOSOLV PTB (propylene glycol tertiary butyl ether), and ARCOSOLV PNP (propylene glycol normal propyl ether).

Preferably, the propylene glycol monoalkyl ether that is purified by the method of the invention is propylene glycol monomethyl ether.

In order to reduce the level of impurities in the propylene glycol monoalkyl ether feed stream, the propylene glycol monoalkyl ether is contacted in the liquid phase with a carbon adsorbent. In accordance with the present invention, the impure propylene glycol monoalkyl ether is contacted in the liquid phase with a carbon adsorbent whereby carbonyl impurities are retained on the carbon adsorbent and a purified propylene glycol monoalkyl ether product reduced in carbonyl impurities content is conveniently separated.

The carbon adsorbent useful in the invention is a solid material that contains a major proportion of carbon. Exceptionally useful carbon adsorbents include activated carbons or charcoals, including those obtained from lignite, gas black, coconut, bagasse, wood, sawdust, peat, pulp-mill waste, blood, bone, etc. Specific commercially available activated carbons include Calgon Corporation's Filtrasorb® 600, SGL®, CPG-LF®, BPL®, and CAL® granular carbons; NORIT granular activated carbons such as NORIT® GAC 830, NORIT® RO 0.8, and Darco® activated carbons; and MeadWestvaco Corporations's Nuchar activated carbons such as Nuchar® WV-B granular activated carbon.

In general, suitable carbon adsorbents are further characterized by having a relatively large surface area in relation to their mass. The carbon adsorbents for purpose of this invention preferably have a surface area of at least 200 m$^2$/g, and more preferably the average surface area is from 400 m$^2$/g to 1500 m$^2$/g.

The carbon adsorbent may be in granular, pelleted, or powdered form. Adsorption is preferably carried out by passing the impure propylene glycol monoalkyl ether through a bed of granular carbon adsorbent or pelleted carbon adsorbent. Alternatively, powdered carbon adsorbent can be slurred in the impure propylene glycol monoalkyl ether and separated by filtration. Granular carbon adsorbent is particularly preferred.

The invention may be carried out in a continuous or batch-wise fashion in accordance with known procedures. Continuous operation is preferred, as is the use of a plurality of adsorbent contact zones. When a plurality of adsorbent contact zones are used, one zone may be in use while adsorbent in a second zone is regenerated. The use of three contact zones is particularly preferred, with two zones in use at the same time, one a lead contact zone and the second a polishing zone, while the third zone is regenerated.

The adsorptive contact is conveniently carried out at moderate temperatures. Suitable temperatures are in the range of about 10° C. to 100° C., preferably 15° C. to 60° C. In general, higher adsorption temperature reduces adsorption capacity. Therefore, to maximize adsorption capacity of the carbon adsorbent, it is preferable to control the adsorption temperature within the range of about 20° C. to 40° C. Flow rates of about 0.005 to 50 volumes of propylene glycol monoalkyl ether per volume of adsorbent per hour are preferred, more preferably about 0.02-5. In general, slower feed flow rate reduces product impurity at a given bed-volume. Therefore, flow rate may be optimized depending on the volume of adsorbent utilized in the method.

The carbon adsorbent retains the impurities adsorbed thereon and purified propylene glycol monoalkyl ether can be separated. Initially, there can be substantially complete removal of the carbonyl impurities and the recovered propylene glycol monoalkyl ether is of exceptional purity. Over the course of time the contact solids gradually become less effective for the removal of these impurities.

Thus, when the separation efficiency of the carbon adsorbent has fallen below a desired point, the carbon adsorbent contact materials are preferably regenerated, as by contact with a heated vapor stream such as nitrogen or air at a temperature of at least 200° C. or by wash with a solvent such as methanol, acetone or water. It is advantageous to employ a plurality of parallel contact zones such that while one zone is being regenerated the feed is passed through a zone containing fresh or regenerated contact material so that optimum impurities removal can be achieved.

Following the purification method, a purified propylene glycol monoalkyl ether product having a decreased carbonyl impurities content is recovered. Preferably, the purified propylene glycol monoalkyl ether product has a UV absorbance, at 245 nm, of 0.5 or less.

The following examples merely illustrate the invention. Those skilled in the art will recognize many variations that are within the spirit of the invention and scope of the claims.

EXAMPLE 1

Adsorption Runs with Activated Carbon

A stainless steel tube (1 inch I.D.×2 ft.) is packed with various activated carbon adsorbents from Calgon Corporation (CAL 12×40, CPG-LF 12×40, SGL 8×30, FILTRASORB 600, APC 12×40, and BPL 6×16). The tube is placed in an electric furnace and the temperature is controlled to 28° C. The feed of propylene glycol monoalkyl ether (containing 73 ppm carbonyl impurities and UV absorbance 1.25) is passed upflow through the bed at a LHSV from 0.7-1 h$^{-1}$ and samples are collected periodically after a total of 2 bed volumes (BV) and 4 BV have passed through the bed. The samples are analyzed for carbonyl content and UV absorbance (at 245 nm). Results are shown in Table 1.

COMPARISON EXAMPLE 2

Comparison Adsorption Runs

Comparison Runs 2A and 2B are run according to the procedure of Example 1, with the exception that activated alumina Selexorb CD 7×14 and Molecular Sieves 13X are used as the adsorbents. Results are shown in Table 1.

TABLE 1

Adsorption Run Data

| Run # | Adsorbent | # BV | Carbonyl Amount (ppm) | UV, abs. |
|---|---|---|---|---|
|  | FEED |  | 73 | 1.25 |
| 1A | CAL 12x40 | 2 | 40 | 0.2 |
|  |  | 4 | 56 | 0.48 |
| 1B | CPG-LF 12x40 | 2 | 29 | 0.19 |
|  |  | 4 | 45 | 0.37 |
| 1C | SGL 8x30 | 2 | 27 | 0.13 |
|  |  | 4 | 35 | 0.26 |
| 1D | Filtrasorb 600 | 2 | 19 | 0.09 |
|  |  | 4 | 33 | 0.11 |
| 1E | APC 12x40 | 2 | 45 | 0.19 |
|  |  | 4 | 57 | 0.54 |
| 1F | BPL 6x16 | 2 | 42 | 0.23 |
|  |  | 4 | 57 | 0.48 |
| 2A* | Activated Alumina Selexorb CD 7x14 | 2 | 70 | 1.20 |
|  |  | 4 | 73 | 1.25 |
| 2B* | Molecular Sieve 13X | 2 | 69 | 1.21 |
|  |  | 4 | 72 | 1.26 |

*Comparative Example

We claim:

1. A method of purifying a propylene glycol monoalkyl ether containing carbonyl impurities which comprises contacting the propylene glycol monoalkyl ether in the liquid phase with a carbon adsorbent, and recovering a purified propylene glycol monoalkyl ether product having a decreased carbonyl impurities content.

2. The method of claim 1 wherein the propylene glycol monoalkyl ether is propylene glycol monomethyl ether.

3. The method of claim 1 wherein the carbon adsorbent is an activated carbon.

4. The method of claim 1 wherein the carbon adsorbent is a granulated activated carbon.

5. The method of claim 1 wherein the carbon adsorbent has a surface area in the range of from about 400 to about 1500 m$^2$/g.

6. The method of claim 1 wherein the propylene glycol monoalkyl ether is produced by the reaction of propylene oxide and an alcohol in the presence of an alkali or alkaline earth metal alkoxide.

7. The method of claim 6 wherein the alcohol is a $C_1$-$C_4$ alcohol.

8. The method of claim 6 wherein the alkali metal alkoxide catalyst is a potassium alkoxide or a sodium alkoxide.

9. The method of claim 1 wherein the purified propylene glycol monoalkyl ether product has a UV absorbance, at 245 nm, of 0.5 or less.

* * * * *